(12) United States Patent
Vijfvinkel et al.

(10) Patent No.: US 8,900,220 B2
(45) Date of Patent: Dec. 2, 2014

(54) EYE SURGICAL INSTRUMENT

(75) Inventors: Gerrit Jan Vijfvinkel, Zuidland (NL);
Claus Ferdinand Eckardt, Bad Homburg (DE)

(73) Assignee: D.O.R.C. Dutch Ophthalmic Research Center (International) B.V., Zuidland (NL)

( * ) Notice: Subject to any disclaimer, the term of this patent is extended or adjusted under 35 U.S.C. 154(b) by 0 days.

(21) Appl. No.: 13/009,601

(22) Filed: Jan. 19, 2011

(65) Prior Publication Data

US 2011/0118711 A1 May 19, 2011

Related U.S. Application Data

(63) Continuation of application No. 11/734,685, filed on Apr. 12, 2007, now Pat. No. 8,162,928.

(30) Foreign Application Priority Data

Apr. 13, 2006 (NL) .................................... 1031588

(51) Int. Cl.
*A61B 18/20* (2006.01)
*A61B 5/00* (2006.01)
*A61B 3/00* (2006.01)
*A61F 9/007* (2006.01)
*A61B 19/00* (2006.01)

(52) U.S. Cl.
CPC ............... *A61B 5/0084* (2013.01); *A61F 9/007* (2013.01); *A61B 2019/5206* (2013.01); *A61B 3/0008* (2013.01)
USPC ................................................ 606/2; 607/88

(58) Field of Classification Search
USPC ........................ 606/2–19; 607/88–94
See application file for complete search history.

(56) References Cited

U.S. PATENT DOCUMENTS

| | | | |
|---|---|---|---|
| 4,102,342 A | 7/1978 | Akiyama | |
| 5,275,593 A | 1/1994 | Easley | |
| 5,478,338 A | 12/1995 | Reynard | |
| 5,588,952 A | 12/1996 | Dandolu | |
| 5,643,253 A | 7/1997 | Baxter | |
| 5,725,514 A * | 3/1998 | Grinblat et al. | 604/294 |
| 6,015,403 A | 1/2000 | Jones | |
| 6,036,678 A | 3/2000 | Giungo | |
| 6,106,162 A | 8/2000 | Mrakovich | |
| 6,494,878 B1 | 12/2002 | Pawlowski | |
| 7,229,202 B2 | 6/2007 | Sander | |
| 7,704,246 B2 | 4/2010 | Connor | |
| 7,783,346 B2 * | 8/2010 | Smith et al. | 604/21 |
| 2003/0169603 A1 | 9/2003 | Luloh | |
| 2005/0245916 A1 | 11/2005 | Connor | |

FOREIGN PATENT DOCUMENTS

WO    WO 98/22805    5/1998

* cited by examiner

*Primary Examiner* — Aaron Roane
(74) *Attorney, Agent, or Firm* — Swanson & Bratschun, L.L.C.

(57) ABSTRACT

An eye surgical instrument, comprising at least one optical fiber for lighting of the interior of the eye, which at least one optical fiber, at a free end thereof, is provided with a light exit and with a stop situated at a distance from the free end, which stop defines an insertion part situated between the end and the stop, and at another end is connectible to a light source, while the stop forms a separate element which is arranged so as to be slidable along the at least one fiber.

11 Claims, 1 Drawing Sheet

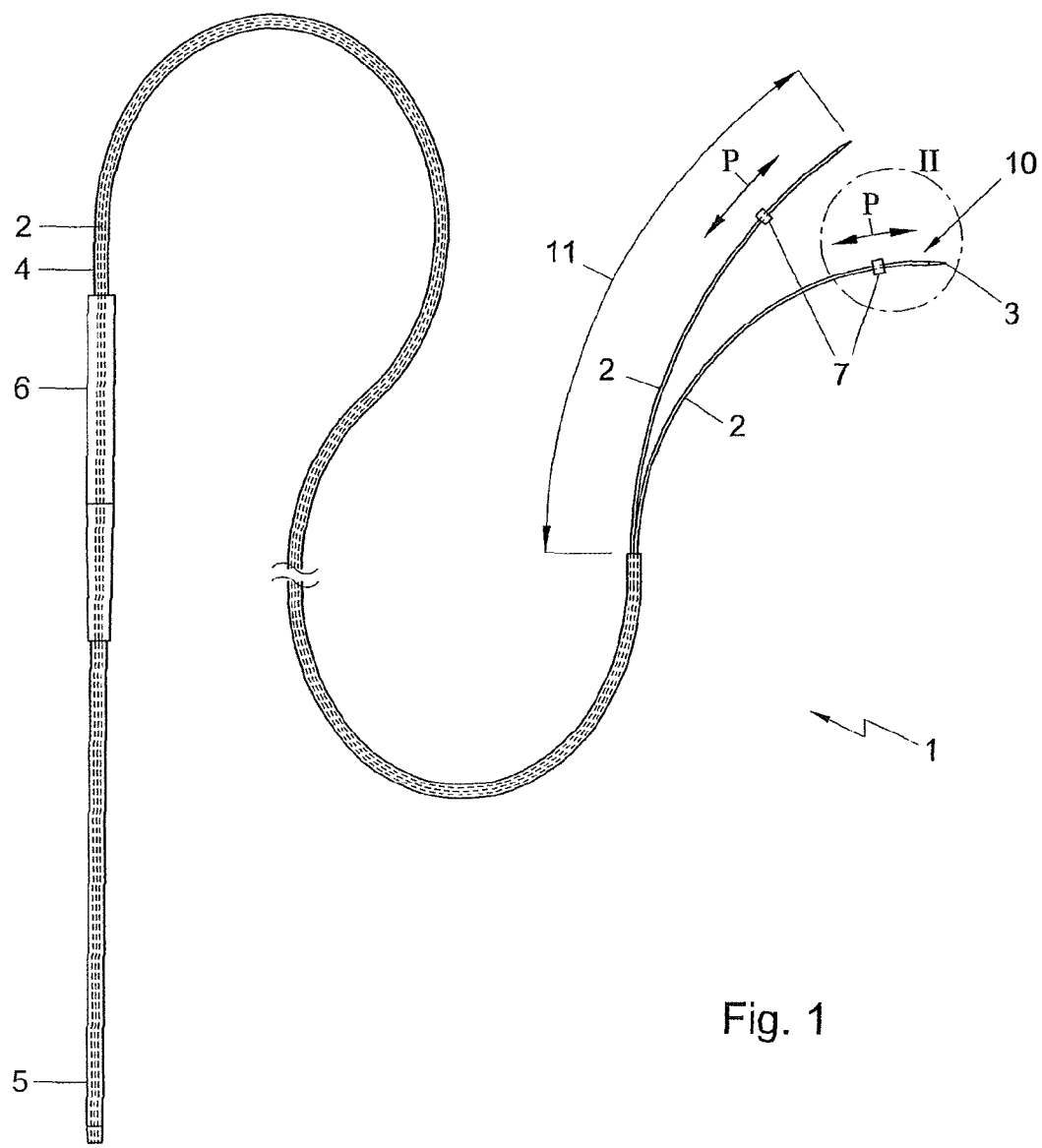
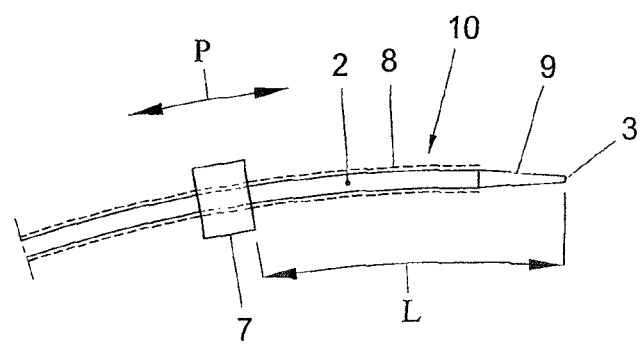

EYE SURGICAL INSTRUMENT

RELATED APPLICATIONS

This application is a continuation of U.S. application Ser. No. 11/734,685, now issued as U.S. Pat. No. 8,162,928, filed Apr. 12, 2007, which claims priority from Netherlands Application No. 1031588, filed Apr. 13, 2006, each entitled "Eye Surgical Instrument," and each of which is hereby incorporated by reference.

TECHNICAL FIELD

This invention relates to an eye surgical instrument for lighting the interior of the eye.

BACKGROUND

Eye surgical instruments with optical fibers for lighting the interior of the eye are known from practice. Multiple fibers in a bundle of fibers are then connected to one light source. Each fiber has a stop, so that an insertion part of the respective fiber, which is to be placed in the eye, can extend a fixed, predetermined distance into the eye. The known fibers are surrounded up to the stop with a sleeve to prevent light exiting. The stop and the sleeve are fixed at a fixed distance to the end of the fibers. In this way, the length of the insertion part will not change while it is fixed in the eye.

One of the disadvantages of this bundle of fibers is that the light often cannot be directed to the desired location in the eye in a precise manner.

This disadvantage and other disadvantages can be counteracted by providing an eye surgical instrument comprising at least one optical fiber for lighting the interior of the eye, which at least one optical fiber is provided at a free end thereof with a light exit and with a stop situated at a distance from the free end, which stop defines an insertion part situated between the end and the stop, and at another end is connectible to a light source, while the stop forms a separate element which is arranged so as to be slidable along the at least one fiber.

With the slidable stop, the length of the insertion part can be adjusted in a simple but precise manner and the light in the eye can be directed better to the desired location in the eye.

The invention is based on the insight that the slidable stop enables more precise directing, while surprisingly, precisely by virtue of the simple and controlled adjustability of the projecting part, a desired safety is maintained.

SUMMARY OF THE EMBODIMENTS

In a preferred embodiment, the stop is arranged to engage the fiber by means of friction. The stop then exerts a frictional force on the fiber, such that the stop can be slid along the fiber with a pair of tweezers.

In another advantageous embodiment, the fiber, adjacent the end thereof, is free of a sleeve over a relatively large part of the length. This creates more sliding room for the stop and so a greater insertion part 10 can be obtained. Preferably, the fiber is further provided with a coating and is relatively thin, for instance of a diameter of less than 0.5 mm. Owing to the free part of the fiber, the coating and/or the small diameter, the fiber and/or the stop can be made of relatively flexible and hence light design.

Further advantageous embodiments of the invention are set forth in the dependent claims.

The invention further relates to a method for adjusting the length of an insertion part of an eye surgical instrument, wherein the instrument comprises at least a light source, a fiber and a stop, wherein the stop is engaged as a separate element with a pair of tweezers and is slid along the fiber.

BRIEF DESCRIPTION OF THE DRAWINGS

The invention will be further elucidated on the basis of an exemplary embodiment which is represented in the drawings. In the drawings:

FIG. 1 shows an eye surgical instrument which is uncoupled from a light source, with a part of the length of the instrument omitted in the drawing;

FIG. 2 shows a detailed representation of the end of a fiber with stop and coating.

DETAILED DESCRIPTION

It is noted that the figures are only schematic representations of a preferred embodiment of the invention, given by way of non-limiting exemplary embodiment. In the drawing, the same or corresponding parts are designated by the same reference numerals.

In FIG. 1 an embodiment of an eye surgical instrument 1 according to the invention is shown which is provided with two optical fibers 2. Each fiber 2 is provided with a free end 3, in this description to be understood as the extreme end of the fiber 2, that is, a point. The eye surgical instrument 1 is further provided with a sleeve 4, to keep the two fibers 2 together over a particular length and to prevent damage and/or contamination of the fibers 2. The eye surgical instrument 1 is further provided with a light source connection 5 for connection of the fibers 2 to a light source, not shown, and a connecting part 6 spanning a part of the connection 5 and of the sleeve 4. Furthermore, the fibers 2 are each provided with a stop 7, slidable along the fibers 2, the sliding directions being indicated by double-headed arrow P.

In FIG. 2 an end of fiber 2 is shown which is situated near the free end 3. As shown, the fiber 2 is surrounded over a part of the length by a coating 8 which makes it possible that no light exits from the fiber 2 until a light exit 9. At the light exit 9 the light transported by the eye surgical instrument 1 exits from the fiber 2. An insertion part 10 of the fiber 2, which in use is preferably placed in the eye over approximately the whole length, is defined by the part of the fiber 2 from the free end 3 to the stop 7.

In use, the insertion part 10 is placed in the respective eye of a patient. To that end, for instance with a needle, one or more relatively small perforations or incisions are formed in the sclera of the eye, after which the insertion part 10 is introduced into a perforation to light the interior of the eye. The length of the insertion part 10 can be adjusted so that the light exit 9 can be moved closer to the location in the eye to be lighted, or further away from it. To this end, for instance before but also during insertion of the insertion part 10 into the eye, the stop 7 can be moved along the fiber 2. One way of sliding the stop 7 characteristically involves retracting the fiber 2 partly out of the eye to some extent but still leaving it in the eye, for instance with one hand, and displacing the stop 7 with the other hand, for instance using a pair of tweezers. The insertion part 10 can thereupon be moved into the eye as far as the stop 7, with the stop 7 engaging the eye. Thus, the position of the stop 7 in effect defines a length L of the insertion part 10.

As shown in FIG. 1, the fiber 2 adjacent the end 3 thereof is free of the sleeve 4 over a relatively large part of the length. This creates a greater sliding range 11 for the stop 7 and hence a larger insertion part 10 can be obtained.

As the stop 7 exerts frictional force on the fiber 2, in common situations the stop 7 will in principle not move along the fiber 2 and the length of the insertion part 10 will in principle not change while it is placed in the eye. On the other hand, the frictional force is of such magnitude as to allow the specialist in question to slide the stop 7 as an independent element along the fiber 2, preferably using a pair of tweezers. For exerting friction on the fiber 2, the stop 7 is preferably manufactured from slightly flexible material.

In an embodiment, the stop 7 is manufactured substantially from silicone material, which material is favorable for application to the eye. In addition, the stop 7 is substantially somewhat ring-shaped, which makes it relatively simple to produce and to slide and moreover gives it good stop properties.

By virtue of the fiber 2 being of very thin design, a small perforation or incision in the sclera of the eye will suffice for insertion of the insertion part 10. This perforation is for instance provided with a relatively thin needle. Small perforations and/or incisions in the eye will typically close up naturally, so that suture is not necessary. Also, such a relatively small perforation can clamp the fiber 2 in place. This has as a consequence, for instance, that in use the insertion part 10 of the fiber 2 does not readily become dislodged from the perforation, for instance when one of the fibers 2 is knocked against.

In particular embodiments, fibers 2 are used that are known from other technical fields such as telecommunication. In telecommunication, for instance fibers 2 with a thin coating 8 are known with which a small diameter is realized. The fiber is for instance manufactured from polymethylmethacrylate of high purity (high purity PMMA), while the thin coating 8 is manufactured, for instance, from fluorinated PMMA. An advantageous embodiment of the eye surgical instrument utilizes such a fiber 2, which fiber 2 inclusive of coating 8 has for instance a diameter of less than 0.5 mm, in particular between 0.2 and 0.4 mm. The thin diameter is enabled inter alia by virtue of the thinly applied coating 8 which ensures that the light does not exit. For additional protection against for instance damage or contamination of the fibers 2, a sleeve 4 can be used which surrounds the fibers 2 with coating 8. The sleeve can extend for instance from a point adjacent the light connection 5 to a point adjacent the end of the fiber 2. In a favorable embodiment, a sufficient distance from the end 3 is maintained, so that the stop 7 can be slid over a sufficiently large distance.

In one embodiment, multiple fibers are provided, so that the interior of the eye can be lighted with multiple light exits 9. Preferably, the eye surgical instrument comprises two or three fibers 2. In this way, a relatively simple, light-weight and safe eye surgical instrument is achieved. As a result of a relatively low weight, the thin fiber 2 will less readily fall out of the eye.

The light exit 9 is preferably tapered at the end. This simplifies insertion of the fiber 2 into the eye. In addition, in this way, there is formed for instance a point light source to be directed. The exit 9 may be arranged for converging and/or diverging light, for instance with a convex or concave form, or be provided with a lens.

Instead of using tweezers, the stop 7 can for instance also be displaced with the fingers, preferably using gloves.

In particular embodiments, a or each fiber 2 may be provided with a fixed stop 7 (not shown), in addition to a slidable one. The fixed stop may be provided, for instance, though by no means exclusively so, at the end of the sleeve 4. It is also possible that a fiber 2 has for instance at least one second stop (not shown either) exerting on the fiber 2 approximately the same frictional force as or a higher frictional force than the stop 7. Optionally, the stop 7 could, if desired, be temporarily removed from the fiber 2, so that only the at least one fixed or second stop remains on the fiber 2. This type of second or fixed stops can provide additional safety against the insertion part 10 possibly shooting through in the eye.

The invention is not limited to the exemplary embodiments represented above. Many variants and combinations thereof or elements thereof are possible.

Such variants and combinations will be clear to those skilled in the art and are understood to fall within the scope of the invention as set forth in the following claims.

What is claimed is:

1. An eye surgical instrument, comprising:
at least one optical fiber for lighting of the interior of the eye, which at least one optical fiber is provided at a free end thereof with a light exit and with a stop situated at a select distance from the free end by frictional force on the fiber, which stop defines an insertion part situated between the free end and the stop and another end thereof is configured for optical association with a light source, the stop being slidable along the length of the at least one fiber, wherein a length of the insertion part can be selectively varied by a user during use of the eye surgical instrument.

2. The instrument according to claim 1 wherein the stop is attached to but is a separate element from the fiber.

3. The instrument according to claim 2, further comprising the stop being an annular element of silicone material which surrounds the fiber.

4. The instrument of claim 1 further comprising a sleeve which at a distance from the stop surrounds a part of the fiber, the sleeve extending to a point on the fiber away from the free end, the sleeve being configured to protect the fiber or the coating from damage.

5. The instrument of claim 4 further comprising more than one fiber being provided in the sleeve.

6. The instrument of claim 1 further comprising a connecting element for cooperation with the light source operatively associated with the other end of the fiber.

7. The instrument of claim 1, wherein the diameter of the at least one fiber is between 0.2 and 0.5 mm.

8. The instrument of claim 1, wherein the diameter of the at least one fiber is between 0.2 and 0.4 mm.

9. The instrument of claim 1, wherein the wherein the stop is slidable so that the length of the insertion part can be selectively varied by a user during use of the eye surgical instrument to place the light exit at any depth within of an interior of an eye.

10. An eye surgical instrument, comprising:
at least one optical fiber for lighting of the interior of the eye, which at least one optical fiber is provided at a free end thereof with a light exit and with a stop situated at a select distance from the free end by frictional force on the fiber, which stop defines an insertion part situated between the free end and the stop and another end thereof is configured for optical association with a light source, the fiber being surrounded up to the light exit by a coating that prevents exit of light, the stop being slidable along the length of the at least one fiber, along the coating, wherein a length of the insertion part can be selectively varied by a user during use of the eye surgical instrument.

11. The instrument of claim 10, wherein the wherein the length of the insertion part can be selectively varied by a user during use of the eye surgical instrument to place the light exit at any depth within of an interior of an eye.

* * * * *